United States Patent
Lee

(10) Patent No.: US 9,682,237 B2
(45) Date of Patent: Jun. 20, 2017

(54) HIGH VOLTAGE MONITORING SUCCESSIVE APPROXIMATION ANALOG TO DIGITAL CONVERTER

(71) Applicant: ALFRED E. MANN FOUNDATION FOR SCIENTIFIC RESEARCH, Santa Clarita, CA (US)

(72) Inventor: Edward K. F. Lee, Fullerton, CA (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 0 days.

(21) Appl. No.: 14/693,740

(22) Filed: Apr. 22, 2015

(65) Prior Publication Data
US 2015/0374997 A1  Dec. 31, 2015

Related U.S. Application Data

(63) Continuation of application No. 14/217,329, filed on Mar. 17, 2014, now Pat. No. 9,044,614.
(Continued)

(51) Int. Cl.
*H03M 1/12* (2006.01)
*A61N 1/36* (2006.01)
(Continued)

(52) U.S. Cl.
CPC ..... *A61N 1/36125* (2013.01); *A61N 1/36071* (2013.01); *A61N 1/37235* (2013.01);
(Continued)

(58) Field of Classification Search
CPC ........... H03M 1/804; H03M 1/12; H03M 1/00
(Continued)

(56) References Cited

U.S. PATENT DOCUMENTS 3,646,940 A  3/1972 Timm et al.
3,942,535 A  3/1976 Schulman et al.
(Continued)

FOREIGN PATENT DOCUMENTS

DE  102010006837 A1  8/2011
EP  1680182  7/2006
(Continued)

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.
(Continued)

*Primary Examiner* — Joseph Lauture
(74) *Attorney, Agent, or Firm* — Kilpatrick Townsend & Stockton LLP

(57) ABSTRACT

A successive approximation ADC made of a low voltage configurable differential amplifier and low voltage logic circuits which can convert a high voltage analog input to a digital equivalent. The differential amplifier can be configured as either an op amp or a comparator depending upon the mode of operation. An input capacitor C1 is switchably coupled to an electrode selected for voltage sampling. A switched capacitor array C2 is coupled across the differential amplifier input and output. A SAR coupled to the switched capacitor array provides a digital output corresponding to the sampled analog voltage. During a sampling interval and a charge transfer interval, the differential amplifier is configured as an op amp. During the transfer interval, the voltage on the input capacitor multiplied by the ratio C1/C2 is transferred to the switched capacitor array. During an
(Continued)

analog to digital conversion interval, the ADC converts the analog voltage to an equivalent digital output.

28 Claims, 6 Drawing Sheets

Related U.S. Application Data

(60) Provisional application No. 61/788,926, filed on Mar. 15, 2013.

(51) Int. Cl.
*A61N 1/372* (2006.01)
*H03M 1/38* (2006.01)
*H03M 1/80* (2006.01)
*H03M 1/00* (2006.01)
*H03M 1/46* (2006.01)
*H03M 1/68* (2006.01)

(52) U.S. Cl.
CPC ............ *H03M 1/129* (2013.01); *H03M 1/38* (2013.01); *H03M 1/00* (2013.01); *H03M 1/12* (2013.01); *H03M 1/468* (2013.01); *H03M 1/685* (2013.01); *H03M 1/804* (2013.01)

(58) Field of Classification Search
USPC ........ 341/172, 155, 156, 118, 120; 600/561; 607/46, 2, 59
See application file for complete search history.

(56) References Cited

U.S. PATENT DOCUMENTS

| | | |
|---|---|---|
| 4,019,518 A | 4/1977 | Maurer et al. |
| 4,044,774 A | 8/1977 | Corbin et al. |
| 4,082,097 A | 4/1978 | Mann et al. |
| 4,340,062 A | 7/1982 | Thompson et al. |
| 4,468,723 A | 8/1984 | Hughes |
| 4,558,702 A | 12/1985 | Barreras et al. |
| 4,673,867 A | 6/1987 | Davis |
| 4,744,371 A | 5/1988 | Harris |
| 5,143,089 A | 9/1992 | Alt |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,835,049 A * | 11/1998 | Nagaraj ............... H03F 3/72 330/9 |
| 5,876,423 A | 3/1999 | Braun |
| 5,877,472 A | 3/1999 | Campbell et al. |
| 6,027,456 A | 2/2000 | Feler et al. |
| 6,035,237 A | 3/2000 | Schulman et al. |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,164,284 A | 12/2000 | Schulman et al. |
| 6,172,556 B1 | 1/2001 | Prentice |
| 6,178,353 B1 | 1/2001 | Griffith et al. |
| 6,185,452 B1 | 2/2001 | Schulman et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,307,497 B1 | 10/2001 | Leung et al. |
| 6,313,779 B1 | 11/2001 | Leung et al. |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,521,350 B2 | 2/2003 | Fey et al. |
| 6,564,807 B1 | 5/2003 | Schulman et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,652,449 B1 | 11/2003 | Gross et al. |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,864,755 B2 | 3/2005 | Moore |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,245,972 B2 | 7/2007 | Davis |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,331,499 B2 | 2/2008 | Jiang et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,496,404 B2 | 2/2009 | Meadows et al. |
| 7,513,257 B2 | 4/2009 | Schulman et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |

(56) References Cited

U.S. PATENT DOCUMENTS

| | | |
|---|---|---|
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,741,981 B1 * | 6/2010 | Wan .............. H03M 1/02 341/110 |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 2002/0116042 A1 | 8/2002 | Boling |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0206166 A1 | 9/2006 | Weiner |
| 2007/0073357 A1 | 3/2007 | Rooney et al. |
| 2007/0265675 A1 | 11/2007 | Lund et al. |
| 2007/0293914 A1 | 12/2007 | Woods et al. |
| 2008/0132961 A1 | 6/2008 | Jaax et al. |
| 2008/0172109 A1 | 7/2008 | Rahman et al. |
| 2008/0183236 A1 | 7/2008 | Gerber |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0184857 A1 | 7/2009 | Furuta et al. |
| 2009/0259273 A1 | 10/2009 | Figueiredo et al. |
| 2010/0076254 A1 | 3/2010 | Jimenez et al. |
| 2010/0076534 A1 | 3/2010 | Mock |
| 2010/0244859 A1 * | 9/2010 | Cormier, Jr. .......... G06F 3/044 324/678 |
| 2011/0043394 A1 * | 2/2011 | Farabegoli .......... H03M 1/1076 341/120 |
| 2011/0152959 A1 | 6/2011 | Sherwood et al. |
| 2011/0270269 A1 | 11/2011 | Swoyer et al. |
| 2011/0278948 A1 | 11/2011 | Forsell |
| 2011/0282416 A1 | 11/2011 | Hamann et al. |
| 2011/0301667 A1 | 12/2011 | Olson et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0130448 A1 | 5/2012 | Woods et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0023958 A1 | 1/2013 | Fell |
| 2013/0096651 A1 | 4/2013 | Ozawa |
| 2013/0150925 A1 | 6/2013 | Vamos et al. |

(56) References Cited

U.S. PATENT DOCUMENTS

| | | |
|---|---|---|
| 2013/0197608 A1 | 8/2013 | Eiger |
| 2013/0207863 A1 | 8/2013 | Joshi |
| 2013/0211479 A1 | 8/2013 | Olson et al. |
| 2013/0303942 A1 | 11/2013 | Damaser et al. |
| 2013/0310894 A1 | 11/2013 | Trier |
| 2013/0331909 A1 | 12/2013 | Gerber |
| 2014/0222112 A1 | 8/2014 | Fell |
| 2014/0237806 A1 | 8/2014 | Smith et al. |
| 2015/0214604 A1 | 7/2015 | Zhao et al. |

FOREIGN PATENT DOCUMENTS

| | | |
|---|---|---|
| EP | 1904153 | 4/2008 |
| EP | 2243509 | 10/2010 |
| JP | 2001108814 A | 4/2001 |
| JP | 2003047179 A | 2/2003 |
| JP | 2011004166 A | 1/2011 |
| JP | 2011114785 A | 6/2011 |
| WO | WO 00-56677 A1 | 3/2000 |
| WO | WO 00-66221 A1 | 11/2000 |
| WO | WO 02/03408 A2 | 1/2002 |
| WO | WO 2004-103465 A1 | 12/2004 |
| WO | WO 2008/021524 | 2/2008 |
| WO | WO 2009-051539 A1 | 4/2009 |
| WO | WO 2009-091267 A2 | 7/2009 |
| WO | WO 2010-042056 A1 | 4/2010 |
| WO | WO 2010-042057 A1 | 4/2010 |
| WO | WO 2011/005607 A1 | 1/2011 |
| WO | WO 2011/059565 | 5/2011 |
| WO | WO 2013/141884 | 9/2013 |

OTHER PUBLICATIONS

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Tanagho, E., et al., Bladder Pacemaker: Scientific Basis and Clinical Future, Urology, Dec. 1982, vol. 20, No. 6, pp. 614-619.

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994 (Jan. 1, 1994), pp. 148-152.

Gundason, G., "A low-power ASK demodulator for Inductively coupled implantable electronics", Solid-State Circuits Conference, 2000, Esscirc "00, Proceedings of the 26rd European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, (Mar. 1, 2005), pp. 763-771.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006 (Dec. 1, 2006), pp. 696-699.

\* cited by examiner

HIGH VOLTAGE MONITORING SUCCESSIVE APPROXIMATION ANALOG TO DIGITAL CONVERTER

This application is a continuation of U.S. application Ser. No. 14/217,329, filed on Mar. 17, 2014, which claims the benefit of U.S. Provisional Application No. 61/788,926, filed on Mar. 15, 2013. The subject matter of the aforementioned applications are hereby incorporated by reference herein in their entirety.

FIELD OF THE INVENTION

The present invention relates to a successive approximation analog to digital converter capable of a broad range of uses and in particular to high voltage stimulation electrode monitoring especially in functional electrical stimulation (FES) applications.

BACKGROUND OF THE INVENTION

Typically in FES applications, current pulses generated in a programmable current generator are applied to nerve tissue for stimulating the tissue through a plurality of selectable electrodes. For many applications, due to the required current pulse amplitudes and the impedance of the stimulated tissue and of the electrodes, a high compliance voltage is required for the stimulators. Compliance voltage is the voltage available at an electrode that can be used to force current to flow through the electrode and still maintain control of the electrode voltage.

In many applications measurements of the electrode voltages are necessary for maintaining the operational integrity of the stimulator circuits. Such samples would be required for example in the measurements and determination of tissue and electrode impedances as well as detecting the existence or absence of shorts or open circuits involving the electrodes. To accommodate digital processing circuitry typically utilized in biomedical devices, digitizing the analog signals normally sensed by the electrodes is often required. However, analog-to-digital converters (ADCs) are often designed using low voltage transistors for minimizing die area as well as power consumption. As a result, the high electrode voltages cannot be digitized directly. Attenuation of the electrode voltage to the input voltage range of the ADC is required.

A common technique to achieve attenuation is to use resistor voltage dividers to divide the high electrode voltage to a lower voltage. However, this technique is not suitable for an FES application since it will draw out current from the stimulator and hence, affecting the stimulation pulse amplitude as well as the output impedance of the stimulator. To alleviate these problems, a voltage buffer between the stimulator and the voltage divider can be added [See Lee, E., "High Voltage Tolerant Stimulation Monitoring Circuit in Conventional CMOS Process", Proc. Of the IEEE 2009 Int. Custom Integrated Circuits Conference (CICC), pp. 93-96, September 2009]. However, such a voltage buffer is difficult to design due to the requirement for a high-voltage rail-to-rail operational amplifier (op amp).

Another possible technique is to use two switched-capacitors (SCs) as two separate resistors to form a voltage divider. In this way, no DC current is drawn out from the stimulator. However, the charge injection of the switches and the nonlinear parasitic capacitances at connection node of the two SCs will affect the accuracy of the attenuation gain as well as the linearity of the divider. Furthermore, an ADC usually has considerable input capacitance. When the ADC input is connected to the SC divider, it will affect the actual attenuation factor of the attenuator. Therefore, instead of using a simple SC voltage divider, a SC amplifier with a voltage gain equal to the required attenuation factor is typically used [See Lee, E., Dai, R., Reeves, N., and Yun, X., "A 36V Biphasic Stimulator with Electrode Monitoring Circuit", Proc. of the 2012 IEEE Int. Symposium on Circuits and Systems, pp 1087-1090, May 2012]. The SC amplifier is not only used for driving the ADC but can also be used for eliminating the parasitic capacitance effects and possibly the charge injection effects. However, this design requires additional power to power the SC amplifier.

Among different ADC architectures, successive approximation ADCs using a SC array digital to analog converter is a popular architecture for biomedical applications since it requires low power consumption for the sampling rate required in most biomedical devices. Based on this type of ADC, one can combine the attenuation function into the ADC. An additional switched-capacitor can be added in series with the SC array at the input of the original ADC architecture [Thomas Paul Kearney, "Programmable Input Range SAR ADC", U.S. Pat. No. 6,731,232]. By properly controlling the clock phases, attenuation can be achieved. Since now the input capacitance of the ADC (capacitance of the SC array) becomes part of the attenuator, no buffer or SC amplifier is required to drive the ADC input. However, the accuracy of the attenuation factor is still affected due to the nonlinear parasitic capacitances and charge injections of the switches. In some instances, what is needed therefore may be a new and novel successive approximation ADC architecture to remedy the deficiencies existing in the art as discussed above.

SUMMARY OF THE INVENTION

One non-limiting embodiment of the present invention includes a differential amplifier configurable as either an op amp or a comparator depending upon the particular mode of operation of the ADC. An input capacitor having a capacitance value of C1 is switchably coupled to an electrode selected for voltage sampling and a second input (negative input) of the differential amplifier. A reference voltage is applied to a first input (positive input) of the differential amplifier. A switched capacitor array having a total capacitance value of C2 is coupled across the second input and the differential amplifier output. The switched capacitor array may be a binary weighted array used for ADC purposes. A successive approximation register is coupled to the switched capacitor array and the differential amplifier output and provides a digital output corresponding to the sampled electrode analog voltage.

In some instances during a sampling interval, the input capacitor is charged to the sampled electrode analog voltage. Concurrently, the differential amplifier is configured as an op amp such that a virtual ground is established at the second input which provides for a path for charging the input capacitor up to the sampled electrode analog voltage.

In some instances during a transfer interval, the voltage on the input capacitor multiplied by the ratio C1/C2 is transferred to the switched capacitor array while the differential amplifier is maintained as being configured as an op amp.

In some instances during an analog to digital conversion interval, the differential amplifier is configured as a comparator and the switched capacitor array, the successive approximation register and the comparator undertake the conversion of the electrode analog voltage to an equivalent digital output.

In one embodiment the present disclosure relates to a peripherally-implantable neurostimulation system. The peripherally implantable neurostimulation system can include a plurality of leads that can each include at least one electrode, an analog-to-digital converter that can include, for example, a successive approximation analog-to-digital converter and an integral switched capacitor amplifier. In some embodiments, the successive approximation analog-to-digital converter and the integral switched capacitor amplifier can share a common differential amplifier. In some embodiments, the system includes a pulse generator that can generate one or several electrical pulses. In some embodiments, the pulse generator is connected to the leads such that the electrical pulses are transmitted to the at least one electrode.

In some embodiments, the peripherally-implantable neurostimulation system can include a successive approximation register. In some embodiments of the peripherally-implantable neurostimulation system, the successive approximation register can include a logic signal generator, which logic signal generator can generate a first signal directing the differential amplifier to operate as an opamp during a first period, and a second signal directing the differential amplifier to operate as a comparator during a second period. In some embodiments, the peripherally-implantable neurostimulation system can include an input capacitor between the leads and the analog-to-digital converter, which input capacitor can be charged during the first period. In some embodiments, the input capacitor can be discharged during the first period and subsequent to the charging of the input capacitor, and the charge the can be transferred to a switched capacitor array.

In one embodiments, the present disclosure relates to an implantable electrical stimulation system. The implantable electrical stimulation system can include a pulse generator that can generate one or several electrical pulses, an electrode array that can output the one or several electrical pulses, an analog-to-digital converter that can convert an analog signal associated with at least one of the electrodes of the electrode array to a digital signal, and that can include a reconfigurable differential amplifier, and a controller that can reconfigure the differential amplifier between an operational amplifier mode and a comparator mode.

In some embodiments of the implantable electrical stimulation system, the analog-to-digital converter can include a successive approximation analog-to-digital converter and a switched capacitor amplifier that share a common differential amplifier. In some embodiments, the implantable electrical stimulation system can include a successive approximation register.

In some embodiments of the implantable electrical stimulation system, the controller can generate a first signal directing the reconfigurable differential amplifier to operate as an opamp during a first period, and a second signal directing the differential amplifier to operate as a comparator during a second period. In some embodiments, the implantable electrical stimulation system can include an input capacitor connecting the leads and the analog-to-digital converter, which input capacitor can be charged during the first period. In some embodiments, the input capacitor is discharged during the first period and subsequent to the charging of the input capacitor, and the charge can be transferred to a switched capacitor array.

In one embodiment, the present disclosure relates to a method of treating neuropathic pain. The method of treating neuropathic pain can include delivering at least one electrical pulse to a body tissue proximate or at a nerve by an implanted pulse generator and at least one electrode, sensing an analog attribute of the at least one electrical pulse using a differential amplifier configured in an operational amplifier mode, and converting the sensed analog attribute to a digital signal using the differential amplifier configured in a comparator mode.

In some embodiments of the method of treating neuropathic pain, delivering the at least one electrical pulse can include delivering at least one electrical pulse to a peripheral body tissue proximate to or at a peripheral nerve. In some embodiments, the electrical pulse can have a first property, which first property can indicate the presence or absence of a short or open circuit and/or the voltage of the at least one electrode. In some embodiments, the method of treating neuropathic pain can include delivering a second electrical pulse having a second property. In some embodiments, the second property of the second electrical pulse can be based on the first property of the electrical pulse and the digital signal.

DETAILED DESCRIPTION OF THE INVENTION

Figure 1:
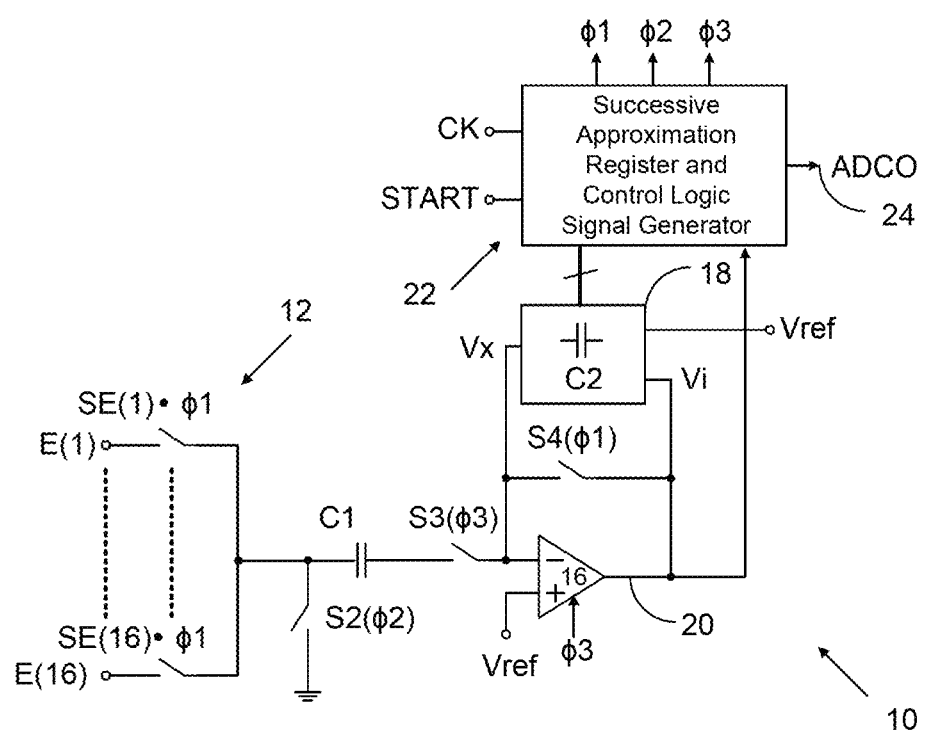
FIG. 1 is a circuit diagram of an embodiment of the ADC of the present invention.

Referring now to FIG. 1, there is shown an overall circuit/block diagram 10 of an embodiment of one embodiment of an analog-to-digital converter (ADC). Specifically, depicted in FIG. 1 is a ten bit ADC architecture that is configured to selectively measure/sample the voltage appearing at sixteen different electrodes. It is to be understood however, that ADC architectures involving fewer or greater than ten bits and sampling of voltages for fewer or greater than sixteen electrodes are within the contemplation of the invention. The electrode voltages to be digitally converted are analog in nature and are individually selected from the electrode array 12 and voltage samples are taken during a sample interval defined when the signal $\phi 1$ is high (See FIG. 2). The selection of the electrode of interest may be determined either by a clinician or programmed in a voltage sample protocol implemented in a processor (not shown). As shown in FIG. 1, the notation SE(j)·$\phi 1$ represents a switch array SE(j) configured as an "and" function switch such that when the E(j) electrode is selected for voltage sample and during the sample interval defined by signal $\phi 1$, the switch SE(j), considered a first switch, is closed and the voltage at the E(j) electrode is measured. In the instance described, the notation (j) is selectable from 1 to 16, however, other embodiments may have more or fewer switches.

The switch array SE(j) is coupled to one input (negative input) of a configurable differential amplifier 16 through a series circuit arrangement with capacitor C1 and a switch S3. A reference voltage Vref is coupled to the other input (positive input) of differential amplifier 16. A second switch S2 is coupled between ground and the interconnection of the switch array SE(j) and capacitor C1. The state of switch S2 is controlled by the signal φ2 and the state of switch S3 is controlled by the signal φ3.

Figure 3:
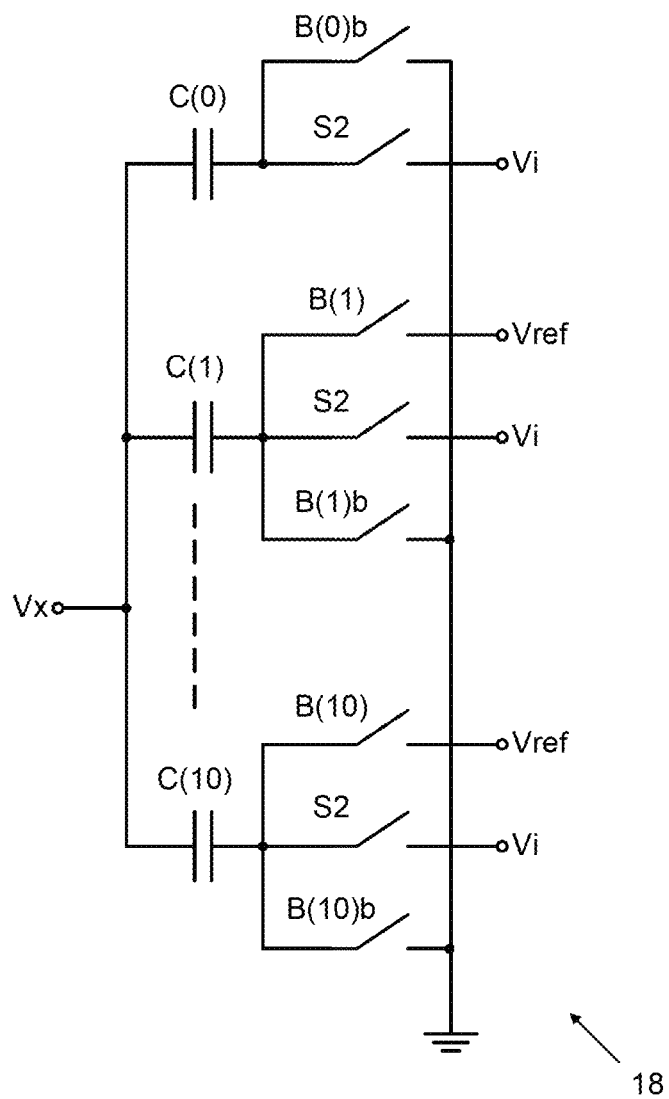
FIG. 3 is a simplified circuit diagram of a conventional switched capacitor array.

A switched capacitor array C2 (18), as shown in FIG. 3, is coupled across an input (negative input) and the output 20 of differential amplifier 16. More specifically, capacitor array 18 may be configured in a binary weighted switched capacitor arrangement so that each capacitor in the array is switchable through a corresponding series switch to be in parallel between a common first port identified as Vx and a common second port identified as Vi. The state of each corresponding series switch S2 is defined by the signal φ2 such that when φ2 is high, all of the capacitors in the array are connected in parallel between the first and second port. In such case, the total capacitance value C2 of the capacitor array 18 is equal to the sum of the capacitance values of all the capacitors in the array. Furthermore, each capacitor is switchable between the first port and a reference voltage identified as Vref in FIG. 3 through a corresponding series switch so that for a 10 bit switched capacitor array, switch B(10) couples the eleventh capacitor C(10) in the array to Vref and switch B(10)b couples the eleventh capacitor C(10) to ground. A similar switching regime is provided for each remaining capacitor in the switched capacitor array 18.

Furthermore, in one embodiment, the 10 bit switched capacitor array 18 of FIG. 3 includes eleven capacitors C(0) to C(11). Capacitor C(0) connected to switch B(0)b, is considered a "dummy" capacitor. The remaining ten capacitors each contribute to forming the ten bit switched capacitor array processing. In terms of a switching protocol for the "B" switches shown in FIG. 3. The following truth table defines the states of the switches as a function of the signals φ1, φ2 and φ3.

TRUTH TABLE FOR "B" SWITCHES IN SWITCHED CAPACITOR ARRAY C2

For φ1 = 1, B(k) = 1 and B(k)b = 0
For φ2 = 1, B(k) = 0 and B(k)b = 0
For φ3 = 0, B(k) and B(k)b are complementary For the above table, "k" varies from 0 to 10

An example of a DAC capacitor array for "n" bits can be found in a technical paper entitled "Capacitor Array Structure and Switch Control for Energy-Efficient SAR Analog-to-Digital Converters" by Jeong-Sup Lee and In-Cheol Park, IEEE Circuits and Systems, 2008. ISCAS 2008. May 18-21, 2008, pp. 236-239. Another reference to switched capacitor arrays appears in "Analog Integrated Circuit Design", by David Johns and Ken Martin, John Wiley & Sons, 1997, pp. 492-496 and therefore operation of the switched capacitor array need not be described in detail.

Figure 2:
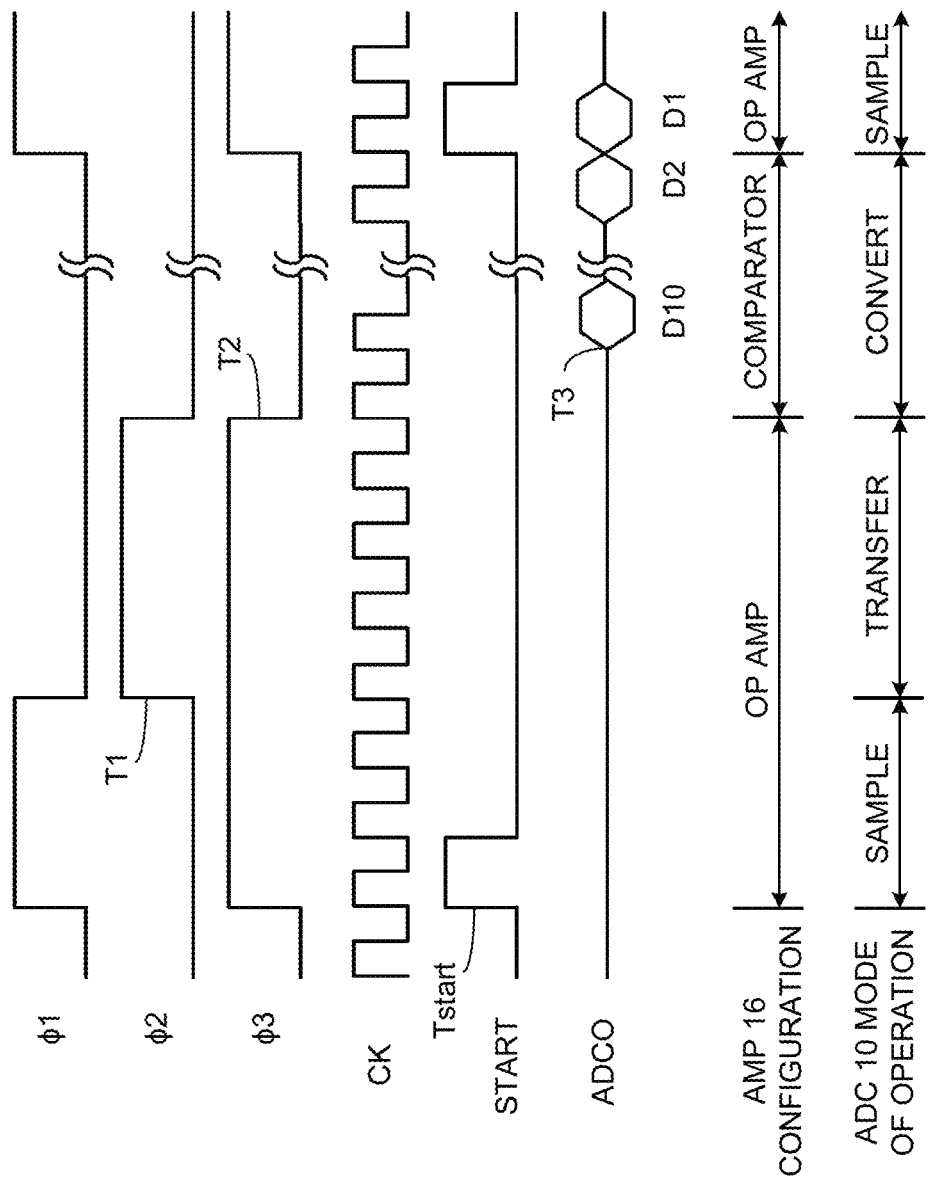
FIG. 2 is a timing diagram of timing control logic signals.

A conventional successive approximation register (SAR) 22 is coupled to the switched capacitor array 18 and to the output 20 of differential amplifier 16. Timing control logic signals φ1, φ2 and φ3 as well as clocking signals CK and a start signal START are generated by a logic signal generator (not shown) contained within SAR 22 and applied for conventional SAR operation. Including the logic signal generator in the SAR 22 tends to reduce overall circuit area but having a logic signal generator outside of the SAR 22 as an independent circuit block is also within the contemplation of the invention. The logic signal generator generates the timing signals φ1, φ2 and φ3 for overall circuit operation. As is shown in FIG. 2, when the signal START goes high or logic "1", the sequence of signals φ1, φ2 and φ3 commence. The output 24 of the SAR 22 is identified as ADCO which represents the converted analog to digital output signal. A switch S4 controlled by signal φ1 is coupled across the output 20 and the negative input of differential amplifier 16 which causes the differential amplifier 16 to function as op amp 16 when φ1 goes high or at logic "1". Additionally, and as is shown in FIG. 1, the signal φ3 is connected directly to differential amplifier 16 in a manner such that when φ3 is high or logic "1", differential amplifier 16 is caused to function as an op amp and when φ3 is low or logic "0" differential amplifier 16 is caused to function as a comparator.

FIG. 2 shows a time line indicating the time intervals during which differential amplifier 16 is configured either as an op amp or a comparator. Also shown in FIG. 2 is a time line indicating the three modes of operation of ADC 10: sampling, transferring or converting an analog input to a digital output. In some embodiments, the three modes of operation of the ADC 10 can correspond to a plurality of periods. In one embodiment, for example, the operation of the ADC 10 can be divided into a first period, wherein sampling and transferring occur, and a second mode, wherein converting of the analog input to the digital output occurs. In one such embodiment, the sampling can occur in a first portion of the first period and the transferring can occur in a second portion of the first period. In one embodiment, for example, the modes of operation of the ADC 10 can be divided into a first period including the sampling, a second period including the transferring, and a third period including the converting of the analog input to the digital output.

In operation, a particular electrode is selected for voltage sampling and switch SE(j), where "j" represents the number of the particular selected electrode, is high or at logic "1". During the sample interval, that is, when the signal φ1 is high or at logic "1", the voltage appearing at the selected electrode E(j) is sampled on capacitor C1. During the sample interval, charge transfers from the selected electrode output to capacitor C1 which causes capacitor C1 to charge up to the electrode output voltage. As noted above, during the sample interval, the configurable differential amplifier 16 functions as an op amp with unity gain feedback by virtue of switch S4 being closed (φ1 being high). By configuring the differential amplifier as an op amp during a sample interval, a virtual ground is established at the differential amplifier second input for facilitating charge transfer from the input capacitor C1 to the switched capacitor array. Furthermore, any voltage offsets (designated as Vos) attributable to op amp 16 are also sampled on capacitor C1. At the same time, the switches B(1) to B(10) are closed such that all the capacitors in the switched capacitor array 18 are coupled to voltage Vref. During the sampling interval, signal φ2 is low so that switch S2 is open and signal φ3 is high so that switch S3 is closed.

During the transfer interval, that is when the signal φ2 is high or logic "1", all the capacitors in the switched capacitor array 18 are coupled to Vi (FIG. 3) which is also coupled to the output 20 of op amp 16. The charge on capacitor C1, as a result of the voltage on C1, is transferred to the switched capacitor array 18 identified as capacitor C2 in FIG. 1, and the voltage across capacitor C2 designated as VC2 is equal to the offset voltage Vos minus the voltage, designated as VE(j), on the "j" electrode, multiplied by the ratio C1/C2 or: VC2=−VE(j)·(C1/C2)+Vos. The voltage VC2 is measured between the first port Vx and the second port Vi of the switched capacitor array 18. As is to be noted and importantly, the voltage appearing on the selected electrode is attenuated by the factor C1/C2 when the capacitance value of capacitor C2 is greater than the capacitance value of capacitor C1. In those instances when it is desired to amplify rather than attenuate the voltage appearing on the selected electrode, the capacitance value of capacitor C1 may be set to be greater than the capacitance value of capacitor C2 so that the ratio of the capacitors equals the desired amplification factor.

It is also to be noted that the symbol C2 has a dual usage such that for purposes of forming the factor C1/C2, the symbol C2 represents the total capacitance value of all the capacitors in the switched capacitor array and for purposes of describing circuit operation, the symbol C2 represents circuit block 18 of FIGS. 1 and 3.

During the transfer interval, the signal φ1 is low so that switch S4 is open and signal φ3 is high so that switch S3 is closed. It is to be noted that during the transfer interval, the capacitors in the switched capacitor array are coupled between the differential amplifier output and the negative input, and are in a feedback loop due to φ2 being high, and differential amplifier 16 remains configured as an op amp.

This new and novel arrangement provides for the measurement of large electrode voltages by first attenuating the high electrode voltage range to a lower voltage range across capacitor C2. The attenuation factor is given precisely by the ratio of capacitors C1 and C2, which (unlike the prior art discussed previously) is not affected by any parasitic capacitance associated with capacitors C1 and C2. Since the voltage across capacitor C2 has a lower voltage range, low voltage circuits including logic circuits can be used for digitizing the voltage across capacitor C2. In addition, since low voltage circuits utilizing low voltage transistors that require small die areas are used, high voltage transistors (that occupy large die areas) are only required for switch S2 as well as the input switch array coupled between the electrode inputs and capacitor C1. As a result, this reduces the overall ADC die area when compared to circuits using high voltage transistors.

During the analog to digital conversion interval, that is when the signal φ3 is low or logic "0", the differential amplifier 16 is configured as a comparator and the voltage VC2 is converted to digital bits (D1 to D10 assuming a 10 bit ADC architecture) in a manner similar to a conventional successive approximation ADC, by switching the capacitors in the switched capacitor array 18 between Vref and ground according to the comparison results generated by comparator 16. For the example 10 bit ADC, although a processor is not shown in the drawings, it is to be understood that a processor configured to undertake the switching activity in the switched capacitor array as well as processing in the successive approximation register (SAR) 22 is within the contemplation of the invention and well within the capabilities of those skilled in the art and therefore is not described here in detail. Upon completion of a successive approximation process during the analog to digital conversion interval, SAR 22 provides the analog to digital converted output at SAR output 24. It is also to be understood that whether done in SAR 22 or after the ADCO (SAR output 24) is generated, the actual converted voltage must be upscaled by the inverse of the attenuation factor C1/C2 or downscaled by the gain factor C1/C2 as the case may be, in order to obtain an accurate conversion of the selected electrode voltage.

With regard to the offset voltage Vos, it is considered that the voltage is unchanged during the sample interval and transfer interval due to proper design of the differential amplifier 16. Moreover, the offset voltage of differential amp 16 is cancelled by the offset voltage stored on capacitor C2.

Figure 4:
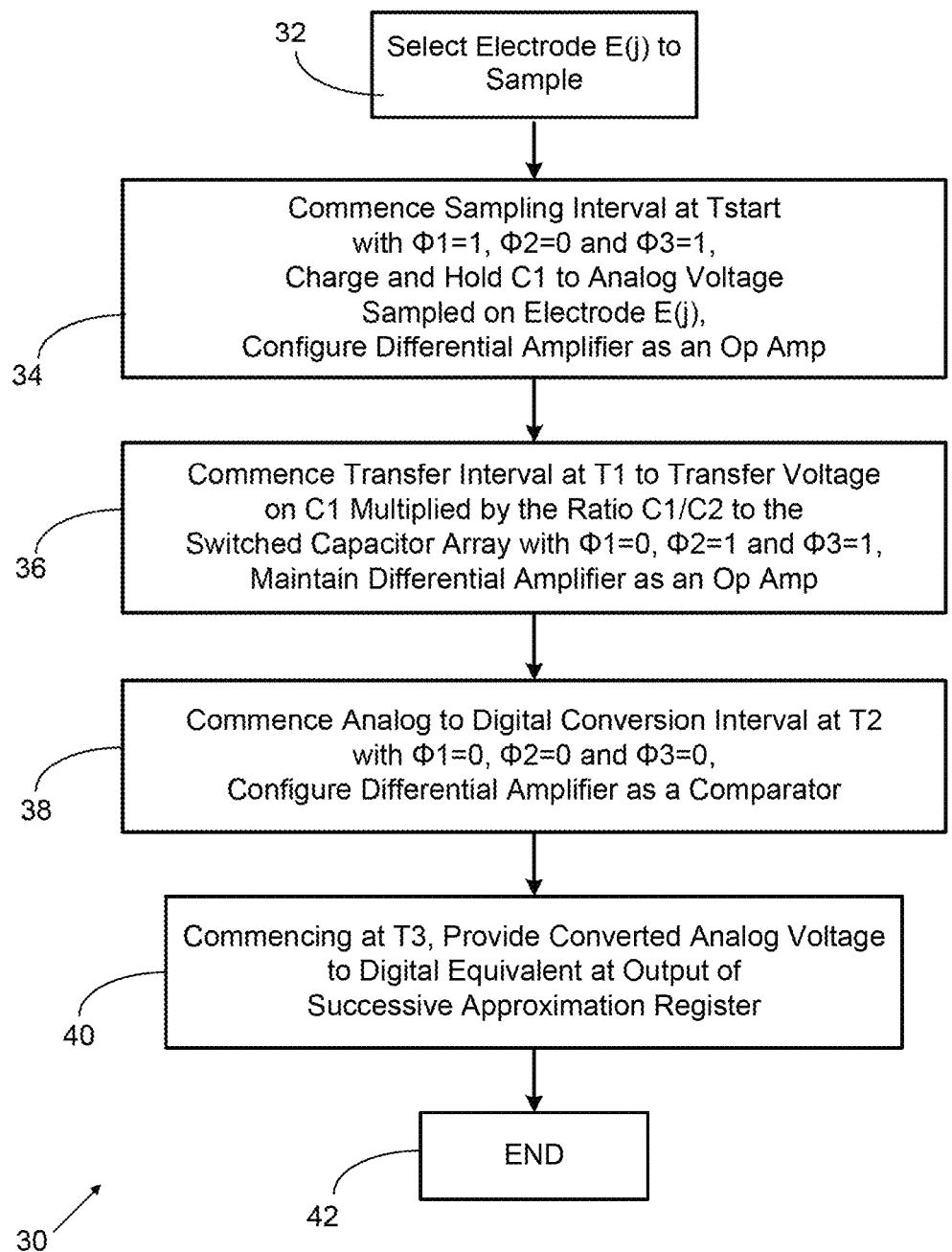
FIG. 4 is a simplified flow chart of the steps involved in the operation of the present invention.

With reference to FIG. 2 and FIG. 4 there are shown a logic signal timing diagram and a flow chart of the ADC process 30 respectively, to convert a sampled selected electrode voltage to its digital equivalent at the output 24 of the SAR 22. At block 32 an electrode from the plurality of electrodes is selected for corresponding analog voltage sampling. At block 34 a voltage sampling interval commences at Tstart and the electrode voltage E(j) is sampled and held on capacitor C1 and the differential amplifier is configured as an op amp. At block 36 a transfer interval commences at T1 and the voltage on C1 multiplied by the ratio C1/C2 is transferred to the switched capacitor array and the differential amplifier is maintained as an op amp. At block 38 an analog to digital conversion commences at T2 and the differential amplifier is configured as a comparator. At T3, at block 40 the converted analog voltage as a digital equivalent is provided at the successive approximation register (SAR 22) output. In some embodiments, information received from the successive approximation register (SAR 22) output can be used to determine the impedance of the electrode and/or tissue surrounding the electrode. In some embodiments, this can be used to determine and/or detect the presence or absence of shorts or open circuits in and/or relating to the electrodes. The process is repeated for other selected electrodes whose analog voltage is to be sampled and converted into a digital equivalent.

In some non-limiting embodiments, the afore described ADC architecture may be incorporated into an implantable electrical stimulation system, such as a peripherally implantable system for treating neuropathic pain.

Approximately 8% of the Western (EU and US) population is affected by Neuropathic pain (chronic intractable pain due to nerve damage). In about 5% of people, this pain is severe. There are at least 200,000 patients that have chronic intractable pain involving a nerve. Neuropathic pain can be very difficult to treat with only half of patients achieving partial relief. Thus, determining the best treatment for individual patients remains challenging. Conventional treatments include certain antidepressants, anti-epileptic drugs and opioids. However, side effects from these drugs can be detrimental. In some of these cases, electrical stimulation, including FES, can provide effect treatment of this pain without the drug-related side effects.

A spinal cord stimulator, which is one type of FES device, is a device used to deliver pulsed electrical signals to the spinal cord to control chronic pain. Because electrical stimulation is a purely electrical treatment and does not cause side effects similar to those caused by drugs, an increasing number of physicians and patients favor the use of electrical stimulation over drugs as a treatment for pain. The exact mechanisms of pain relief by spinal cord stimulation (SCS) are unknown. The scientific background of the SCS trials was based initially on the Gate Control Theory of pain that was first described by Melzack and Wall in 1965. The theory posits that pain is transmitted by two kinds of afferent nerve fibers. One is the larger myelinated Aδ fiber, which carries quick, intense-pain messages. The other is the smaller, unmyelinated "C" fiber, which transmits throbbing, chronic pain messages. A third type of nerve fiber, called Aβ, is "non-nociceptive," meaning it does not transmit pain stimuli. The gate control theory asserts that signals transmitted by the Aδ and C pain fibers can be thwarted by the activation/stimulation of the non-nociceptive Aβ fibers and thus inhibit an individual's perception of pain. Thus, neurostimulation provides pain relief by blocking the pain messages before they reach the brain.

At the present time, SCS is used mostly in the treatment of failed back surgery syndrome, a complex regional pain syndrome that has refractory pain due to ischemia. SCS complications have been reported in 30% to 40% of all SCS patients. This increases the overall costs of patient pain management and decreases the efficacy of SCS. Common complications include: infection, hemorrhaging, injury of nerve tissue, placing device into the wrong compartment, hardware malfunction, lead migration, lead breakage, lead disconnection, lead erosion, pain at the implant site, generator overheating, and charger overheating. The occurrence rates of common complications are surprisingly high: 9.5% are accounted for lead extension connection issues, 6% are due to lead breakage, 22.6% of cases are associated with lead migration and 4.5% experienced infection.

Peripheral neuropathy may be either inherited or acquired. Causes of acquired peripheral neuropathy include physical injury (trauma) to a nerve, viruses, tumors, toxins, autoimmune responses, nutritional deficiencies, alcoholism, diabetes, and vascular and metabolic disorders. Acquired peripheral neuropathies are grouped into three broad categories: those caused by systemic disease, those caused by trauma, and those caused by infections or autoimmune disorders affecting nerve tissue. One example of an acquired peripheral neuropathy is trigeminal neuralgia, in which damage to the trigeminal nerve (the large nerve of the head and face) causes episodic attacks of excruciating, lightning-like pain on one side of the face.

A high percentage of patients with peripheral neuropathic pain do not benefit from SCS for various reasons. However, many of these patients can receive acceptable levels of pain relief via direct electrical stimulation to the corresponding peripheral nerves. This therapy is called peripheral nerve stimulation (PNS). There is, however, no FDA approved PNS devices in the US market. Standard spinal cord stimulator (SCS) devices are often used off label by pain physicians to treat this condition. It is estimated that about 15% of SCS devices have been used off-label for PNS.

As current commercially-available SCS systems were designed for stimulating the spinal cord and not for peripheral nerve stimulation, there are more device complications associated with the use of SCS systems for PNS than for SCS. Current SCS devices (generators) are large and bulky. In the event that an SCS is used for PNS, the SCS generator is typically implanted in the abdominal or in the lower back above the buttocks and long leads are tunneled across multiple joints to reach the target peripheral nerves in the arms, legs or face. The excessive tunneling and the crossing of joints leads to increased post-surgical pain and higher device failure rates. Additionally, rigid leads can lead to skin erosion and penetration, with lead failure rates nearing 100% within 3 years of implantation. Most complications result in replacement surgery and even multiple replacement surgeries in some cases.

Figure 5:
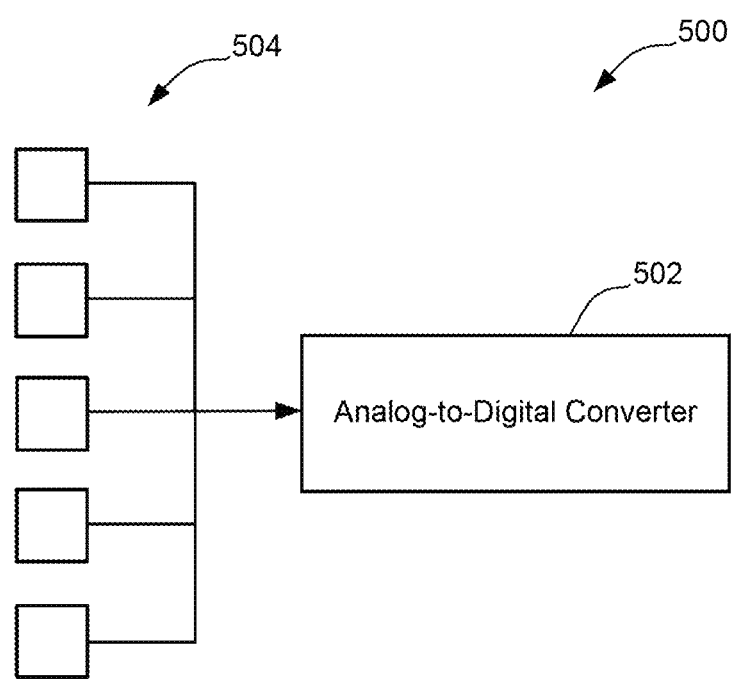
FIG. 5 is a schematic illustration of one embodiment of a sensing system.

One embodiment of a sensing system 500 of a peripherally-implantable neurostimulation system is shown in FIG. 5. In some embodiments, components of the sensing system 500 can be located in other components of the peripherally-implantable neurostimulation system, or can be shared with other components of the peripherally implantable neurostimulation system. In some embodiments, the sensing system 500 can be configured to determine one or several voltages, which can include, measuring/sampling voltage at one or several electrodes. In the embodiment depicted in FIG. 5, the sensing system 500 includes an analog-to-digital converter 502 that is connected to a plurality of electrodes 504. In some embodiments, the analog-to-digital converter 502 can be any circuit configured to sense the full-range of voltages at the electrodes 504 and/or to sense a desired portion of the full-range of the voltages at the electrodes 504, and can be, for example, circuit 10 depicted in FIG. 1.

In some embodiments, the analog-to-digital converter 502 can include one or several space saving features. In one embodiment, for example, the analog-to-digital converter 502 can include one or several switched capacitors, which can be, for example, part of a switched capacitor amplifier. In one embodiment, the switched capacitor amplifier can be combined with a successive approximation analog-to-digital converter, which successive approximation analog-to-digital converter can include a comparator. The combination of the switched capacitor amplifier and the successive approximation analog-to-digital converter is shown in FIG. 1. As seen in FIG. 1, the switched capacitor amplifier is created during time intervals and/or periods when the differential amplifier 16 operates as an opamp. In one such embodiment, the switched capacitor amplifier and the successive approximation analog-to-digital converter can share a common differential amplifier configurable as either an opamp or as a comparator. In one such embodiment, the comparator of the successive approximation analog-to-digital converter can be used as an opamp when the analog-to-digital converter 502 is sampling, and the comparator of the successive approximation analog-to-digital converter can be used as a comparator for the digitization of the measured voltage.

As seen in FIG. 5, the analog-to-digital converter 502 can be connected to a plurality of electrodes 504. In some embodiments, the electrodes 504 can be part of the electrode array 12 shown in FIG. 1. In some embodiments, the electrodes 504 can comprise a conductive portion of one or more leads, such as, for example, a conductive portion of an anodic lead and/or a cathodic lead. In some embodiments, a single electrode 504 can be located on a lead, and in some embodiments, a plurality of electrodes 504 can be located on one lead. The electrodes 504 can, in some embodiments, be placed on, or implanted in a body adjacent to, for example, a nerve. In some embodiments, information identifying the presence or absence of a short or open circuit and/or indicating the voltage of one or several electrodes 504 can be used to alter the creation of one or several electrical pulses and/or pulse patterns.

Figure 6:
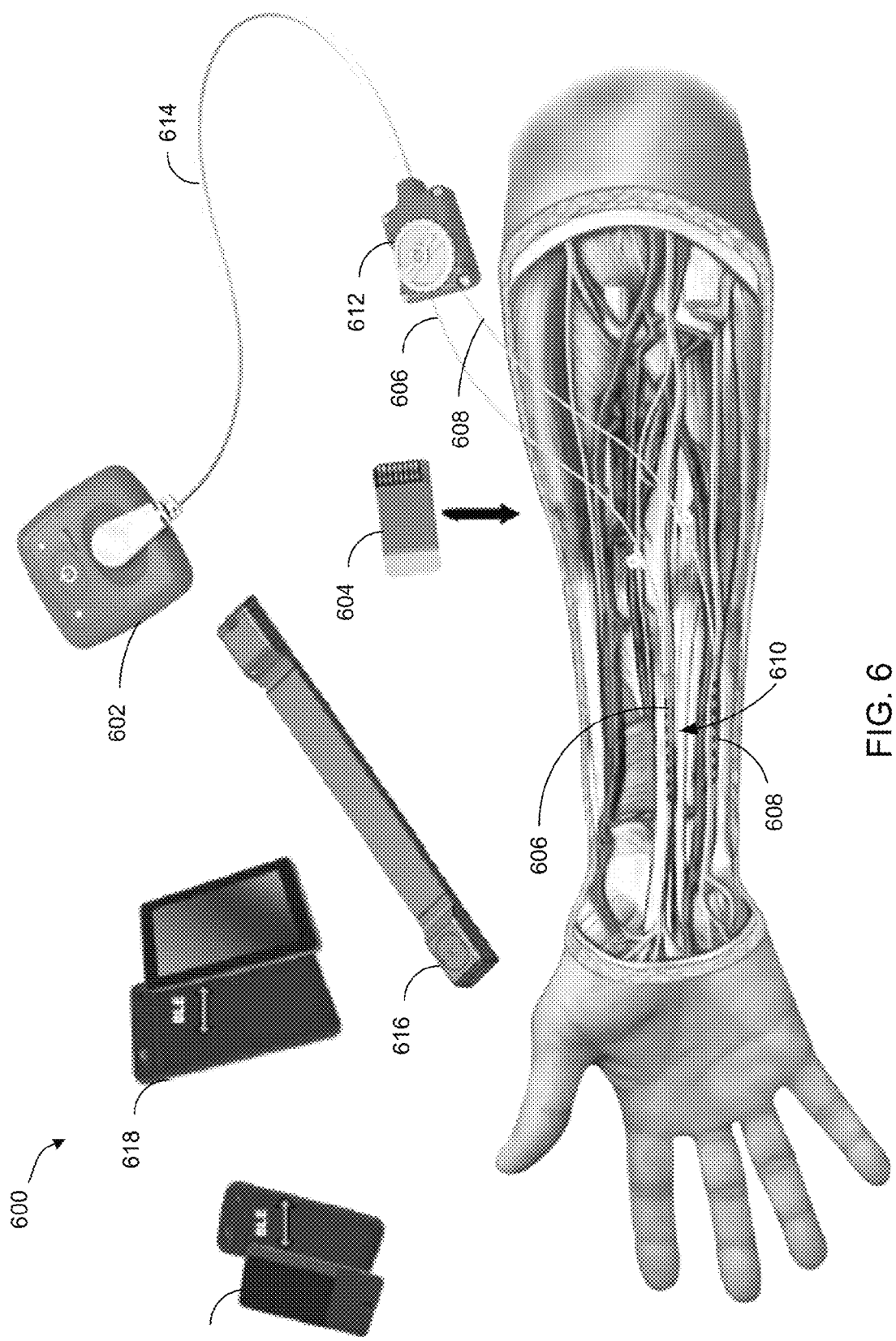
FIG. 6 is a schematic illustration of one embodiment of a peripherally-implantable neurostimulation system.

One embodiment of a peripherally-implantable neurostimulation system 600 is shown in FIG. 6. In some embodiments, the peripherally-implantable neurostimulation system 600 can be used in treating patients with, for example, chronic, severe, refractory neuropathic pain originating from peripheral nerves. In some embodiments, the peripherally-implantable neurostimulation system 600 can be used to either stimulate a target peripheral nerve or the posterior epidural space of the spine.

The peripherally-implantable neurostimulation system 600 can include one or several pulse generators. The pulse generators can comprise a variety of shapes and sizes, and can be made from a variety of materials. In some embodiments, the one or several pulse generators can generate electrical pulses that are delivered to a nerve to control pain. In some embodiments, a pulse generator can be an external pulse generator 602 or an implantable pulse generator 604. In some embodiments, an external pulse generator 602 can be used to evaluate the suitability of a patient for treatment with the peripherally-implantable neurostimulation system 600 and/or for implantation of an implantable pulse generator 604.

The implantable pulse generator 604 can be sized and shaped, and made of material so as to allow implantation of the implantable pulse generator 604 inside of a body. In some embodiments, the implantable pulse generator 604 can be sized and shaped so as to allow placement of the implantable pulse generator 604 at any desired location in a body, and in some embodiments, placed proximate to a peripheral nerve such that leads (discussed below) are not tunneled across joints and/or such that extension cables are not needed. In some embodiments, the pulse generator, and specifically the implantable pulse generator 604 and/or the external pulse generator 602 can incorporate the sensing system of FIG. 5, and specifically, circuit 10 of FIG. 1.

In some embodiments, the electrical pulses generated by the pulse generator can be delivered to one or several nerves 610 and/or to tissue proximate to one or several nerves 610 via one or several leads. The leads can include conductive portions, referred to as electrodes, and non-conductive portions. The leads can have a variety of shapes, can be in a variety of sizes, and can be made from a variety of materials, which size, shape, and materials can be dictated by the application or other factors.

In some embodiments, the leads can include an anodic lead 606 and/or a cathodic lead 608. In some embodiments, the anodic lead 606 and the cathodic lead 608 can be identical leads, but can receive pulses of different polarity from the pulse generator.

In some embodiments, the leads can connect directly to the pulse generator, and in some embodiments, the leads can be connected to the pulse generator via a connector 612 and a connector cable 614. The connector 612 can comprise any device that is able to electrically connect the leads to the connector cable 614. Likewise, the connector cable can be any device capable of transmitting distinct electrical pulses to the anodic lead 606 and the cathodic lead 608.

In some embodiments, the peripherally-implantable neurostimulation system 600 can include a charger 616 that can be configured to recharge the implantable pulse generator 604 when the implantable pulse generator 604 is implanted within a body. The charger 616 can comprise a variety of shapes, sizes, and features, and can be made from a variety of materials. In some embodiments, the charger 616 can recharge the implantable pulse generator 604 via an inductive coupling.

In some embodiments, one or several properties of the electrical pulses can be controlled via a controller. In some embodiments, these properties can include, for example, the frequency, strength, pattern, duration, or other aspects of the timing and magnitude of the electrical pulses. In one embodiment, these properties can include, for example, a voltage, a current, or the like. In one embodiment, a first electrical pulse can have a first property and a second electrical pulse can have a second property. This control of the electrical pulses can include the creation of one or several electrical pulse programs, plans, or patterns, and in some embodiments, this can include the selection of one or several pre-existing electrical pulse programs, plans, or patterns. In the embodiment depicted in FIG. 6, the peripherally-implantable neurostimulation system 600 includes a controller that is a clinician programmer 618. The clinician programmer 618 can be used to create one or several pulse programs, plans, or patterns and/or to select one or several of the created pulse programs, plans, or patterns. In some embodiments, the clinician programmer 618 can be used to program the operation of the pulse generators including, for example, one or both of the external pulse generator 602 and the implantable pulse generator 604. The clinician programmer 618 can comprise a computing device that can wiredly and/or wirelessly communicate with the pulse generators. In some embodiments, the clinician programmer 618 can be further configured to receive information from the pulse generators indicative of the operation and/or effectiveness of the pulse generators and the leads.

In some embodiments, the controller of the peripherally-implantable neurostimulation system 600 can include a patient remote 620. The patient remote 620 can comprise a computing device that can communicate with the pulse generators via a wired or wireless connection. The patient remote 620 can be used to program the pulse generator, and in some embodiments, the patient remote 620 can include one or several pulse generation programs, plans, or patterns created by the clinician programmer 618. In some embodiments, the patient remote 620 can be used to select one or several of the pre-existing pulse generation programs, plans, or patterns and to select, for example, the duration of the selected one of the one or several pulse generation programs, plans, or patterns.

Advantageously, the above outlined components of the peripherally-implantable neurostimulation system 600 can be used to control and provide the generation of electrical pulses to mitigate patient pain.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein. For example, although certain electronic devices were described as being coupled to specific positive and negative inputs of the differential amplifier it is to be understood that other connection assignments for such electronic devices is contemplated by the invention with corresponding adjustments made to logic signal timing and signal processing to achieve desired ADC operation.

What is claimed is:

1. An analog to digital converter (ADC) comprising:
   a switched capacitor array having a total capacitance value of C2;
   a differential amplifier selectably configurable as either an operational amplifier or a comparator, said differential amplifier having first and second inputs and an output, wherein the first input is coupled to a reference voltage and wherein the switched capacitor array is coupled across the second input and the output of the differential amplifier;
   an input capacitor switchably coupled between the differential amplifier second input and an analog voltage source adapted to provide an analog voltage signal to be converted to a digital output signal, said input capacitor having a capacitance value of C1;
   a successive approximation register coupled to the switched capacitor array and the differential amplifier output and configured to provide the digital output signal; and
   a logic signal generator configured to provide timing control logic signals to the other components of the ADC.

2. The ADC of claim 1, wherein the logic signal generator is arranged to charge the input capacitor to a value of the analog voltage signal and configure the differential amplifier as an operational amplifier during a sampling interval such that a virtual ground is established at the differential amplifier second input for facilitating charge transfer from the input capacitor to the switched capacitor array.

3. The ADC of claim 2, wherein the logic signal generator is arranged to transfer the analog voltage signal on the input capacitor multiplied by a ratio C1/C2 to the capacitor array during a transfer interval.

4. The ADC of claim 3, wherein the logic signal generator is arranged to configure the differential amplifier as a comparator for comparing the reference voltage to the voltage on the switched capacitor array, wherein capacitors in the switched capacitor array are switched for converting the voltage on the capacitor array to digital output bits for storage in the successive approximation register according to a comparator output in a successive approximation protocol during an analog to digital conversion interval to thereby provide the digital output signal.

5. The ADC of claim 1, wherein the switched capacitor array is coupled to the input capacitor via the differential amplifier such that a voltage transferred from the input capacitor to the switched capacitor array changes according to a ratio C1/C2.

6. The ADC of claim 5, wherein the capacitance value of C2 is greater than the capacitance value of C1.

7. The ADC of claim 1, wherein the timing control logic signals comprise a first logic signal for controlling a sampling interval, a second logic signal for controlling a transfer interval and a third logic signal for controlling an analog to digital conversion interval, wherein said first, second and third logic signals have logic states "1" and "0", wherein switches controlled by respective first, second and third logic signals are closed when the respective controlling logic signal is at a logic "1" and open when the respective controlling logic signal is at a "0".

8. The ADC of claim 7 further comprising a first switch controlled by the first logic signal and configured to switchably couple the analog voltage signal to the input capacitor.

9. The ADC of claim 8 further comprising a second switch controlled by the second logic signal and configured to switchably couple said input capacitor to ground.

10. The ADC of claim 9 further comprising a third switch controlled by the third logic signal and configured to switchably couple, through said input capacitor, the analog voltage signal to the differential amplifier second input.

11. The ADC of claim 10 further comprising a fourth switch controlled by the first logic signal and configured to couple the differential amplifier output to the differential amplifier second input so as to configure the differential amplifier as an op amp when the first logic signal is at logic "1".

12. The ADC of claim 11 wherein the second switch is rated for a higher voltage than at least one of the first switch, the third switch, and the fourth switch.

13. An analog to digital converter comprising:
a successive approximation analog-to-digital converter;
an integral switched capacitor amplifier; and
a differential amplifier comprising a negative input and a positive input, wherein the successive approximation analog-to-digital converter and the integral switched capacitor amplifier share the differential amplifier via connection to the negative input of the differential amplifier.

14. The analog to digital converter of claim 13, further comprising a successive approximation register.

15. The analog to digital converter of claim 14, wherein the successive approximation register comprises a logic signal generator.

16. The analog to digital converter of claim 15, wherein the logic signal generator is configured to generate a first signal directing the differential amplifier to operate as an opamp during a first period, and a second signal directing the differential amplifier to operate as a comparator during a second period.

17. The analog to digital converter of claim 16, further comprising an input capacitor coupled to the successive approximation analog-to-digital converter and the integral switched capacitor amplifier, wherein the input capacitor is charged during the first period.

18. The analog to digital converter of claim 17, wherein the input capacitor is discharged during the first period and subsequent to the charging of the input capacitor, and wherein the charge is transferred to a switched capacitor array.

19. A system comprising:
an analog-to-digital converter configured to convert an analog signal to a digital signal, the analog-to-digital converter including:
a differential amplifier comprising a positive input, a negative input, and an output, wherein the negative input is electrically coupled to an input capacitor, wherein the negative input and the output are electrically coupled to a switched capacitor array, wherein the differential amplifier is reconfigurable between an operational amplifier mode and a comparator mode; and
a controller configured to reconfigure the differential amplifier between the operational amplifier mode and the comparator mode.

20. The system of claim 19, wherein the analog-to-digital converter comprises a successive approximation analog-to-digital converter and a switched capacitor amplifier that share the differential amplifier.

21. The system of claim 20, further comprising a successive approximation register.

22. The system of claim 19, wherein the controller is configured to generate a first signal directing the differential amplifier to operate as an opamp during a first period, and a second signal directing the differential amplifier to operate as a comparator during a second period.

23. The system of claim 22, wherein the input capacitor is charged during the first period.

24. The system of claim 23, wherein the input capacitor is discharged during the first period and subsequent to the charging of the input capacitor, and wherein the charge is transferred to the switched capacitor array.

25. A method of converting an analog signal to a digital equivalent signal, comprising:
sensing an analog attribute of an analog signal using a differential amplifier configured in an operational amplifier mode, wherein the differential amplifier comprises a positive input, a negative input, and an output, wherein the negative input is electrically coupled to a sampling capacitor, and wherein the negative input and the output are electrically coupled to a switched capacitor array; and
converting the sensed analog attribute to a digital signal using the differential amplifier configured in a comparator mode.

26. The method of claim 25, wherein the digital signal indicates a presence or an absence of a short or open circuit.

27. The method of claim 26, wherein the analog attribute of the analog signal comprises a voltage.

28. The method of claim 27, wherein sensing the analog attribute of the analog signal using the differential amplifier configured in the operational amplifier mode comprises:
    sampling an electrode to charge an input capacitor to the voltage of the analog signal; and
    transferring the voltage from the input capacitor to the switched capacitor array.

\* \* \* \* \*